(12) United States Patent
Blouin (10) Patent No.: US 9,921,139 B1
(45) Date of Patent: Mar. 20, 2018

(54) HANDHELD, UNDERWATER SUCTION SAMPLER

(71) Applicant: Marc A. Blouin, Safety Harbor, FL (US)

(72) Inventor: Marc A. Blouin, Safety Harbor, FL (US)

(73) Assignee: The United States of America as Represented by the Secretary of the Department of the Interior, Washington, DC (US)

( * ) Notice: Subject to any disclaimer, the term of this patent is extended or adjusted under 35 U.S.C. 154(b) by 538 days.

(21) Appl. No.: 14/071,968

(22) Filed: Nov. 5, 2013

Related U.S. Application Data (63) Continuation-in-part of application No. 12/899,330, filed on Oct. 6, 2010, now abandoned.

(51) Int. Cl.
    *G01N 1/14* (2006.01)
(52) U.S. Cl.
    CPC ..................... *G01N 1/14* (2013.01)
(58) Field of Classification Search
    CPC .......... G01N 1/14; G01N 1/24; G01N 1/2273; G01N 33/18
    USPC ...................................................... 73/864.34
    See application file for complete search history.

(56) References Cited

U.S. PATENT DOCUMENTS

| | | | |
|---|---|---|---|
| 3,184,878 A | 5/1965 | Senne | |
| 3,231,997 A | 2/1966 | Shugarman | |
| 3,239,311 A * | 3/1966 | Luehrmann | G01N 27/626 422/54 |
| 4,137,772 A | 2/1979 | Hitch | |
| 4,239,019 A | 12/1980 | Andrews | |
| 4,754,654 A | 7/1988 | Johnson et al. | |
| 4,894,942 A | 1/1990 | Winkler | |
| 5,269,659 A * | 12/1993 | Hampton | F04B 49/06 417/12 |
| 5,500,369 A | 3/1996 | Kiplinger | |
| 5,551,311 A | 9/1996 | Ogden et al. | |
| 6,306,350 B1 | 10/2001 | Mereish et al. | |

(Continued)

OTHER PUBLICATIONS

Brown, A. V., M. D. Schram and P. P. Brussock. 1987. A vacuum benthos sampler suitable for diverse substrates. Hydrobiologia 153: 241-247.

(Continued)

*Primary Examiner* — Helen Kwok
*Assistant Examiner* — Nashmiya Fayyaz
(74) *Attorney, Agent, or Firm* — James Mitchell (57) ABSTRACT

A portable, hand-held sampler for collection of aquatic biotic samples. A pump with an exhaust tube and a water intake tube is attached to a frame. A battery is attached to the frame and electrically connected to the pump. A handle is attached to the bottom of the frame for an operator to hold the sampler in one hand. A switch is electrically connected to the pump and to the battery and attached to the frame near the handle for the operator to control activation of the pump with the same single hand. A venturi tube assembly with a sample intake tube is attached to the exhaust tube. The pump draws water into the water intake tube and sample material into the sample intake tube and the venturi tube diverts the sample material away from the pump and into a sample collection reservoir to prevent damage to the sample material.

18 Claims, 9 Drawing Sheets

(56) References Cited

U.S. PATENT DOCUMENTS

| 2008/0250878 | A1 | 10/2008 | Montefusco |
| 2010/0104473 | A1 | 4/2010 | Kirollos et al. |
| 2015/0177212 | A1* | 6/2015 | Thomas ................ B63G 8/001 114/331 |

OTHER PUBLICATIONS

Davies, I. J., and D. J. Ramsey. 1989. A diver operated suction gun and collection bucket for sampling crayfish and other aquatic macroinvertebrates. Can. J. Aquat. Sci. 46:923-927.

Flath, L. E., and J. A. Dorr III. 1984. A portable, diver-operated, underwater pumping device. Prog. Fish-Cult. 46 (3):219-220.

Kennelly, S.J., and A. J. Underwood. 1985. Sampling of small invertebrates on natural hard substrata in a sublittoral kelp forest. J. Exp. Mar. Biol. Ecol. 89:55-67.

Miles, E. L., and R. B. Whitlatch. 1997. "Priscilla": A portable in situ suction sampling device. In: Diving for Science 1997, American Academy of Underwater Sciences Symposium, Boston, MA; pp. 117-121.

Tanner, C., M. W. Hawkes, P. A. Lednik, and E. Duffield. 1977. A hand-operated suction sampler for the collection of subtidal organisms. J. Fish. Res. Board Can. 34:1031-1034.

Wellnitz, T. A. 1991. A continuous suction device for collecting aquatic insects. J. Freshwat. Ecol. vol. 6(2) pp. 223-225.

Wilcox, J. R., R. P. Meek and D. Mook. 1974. A pneumatically operated slurp gun. Limnol. & Oceanogr. vol. 19(2) pp. 354-355.

* cited by examiner

FIG. 9 ed into the intake tube. The sample collection reservoir is connected to the pump to hold the sample material drawn

HANDHELD, UNDERWATER SUCTION SAMPLER

CROSS-REFERENCE TO RELATED APPLICATION(S)

This application is a continuation-in-part of U.S. patent application Ser. No. 12/899,330, filed on Oct. 6, 2010, which is hereby incorporated by reference in its entirety.

STATEMENT OF GOVERNMENT INTEREST

The invention described herein may be manufactured, used, and licensed by or for the U.S. Government for governmental purposes without payment of any royalties thereon.

BACKGROUND

This application relates to underwater samplers and, in particular, to an improved suction sampler for collecting underwater biological specimens.

Underwater suction samplers have been used to collect samples of small aquatic flora and fauna. Unfortunately, sampling has been inconvenient or unsafe for divers using these types of samplers. For example, some samplers have limited mobility during operation due to their size and/or weight. Some samplers are heavy, or large and bulky, requiring two or more persons for transportation and operation. Some samplers weigh more than 8 lbs in water and 31 lbs in air and are more than 685 mm in length. Some of the large and heavy samplers cannot even be used by divers.

Other samplers lack mobility during operation because the body of the sampler or a component of the sampler must be placed on the bottom of the body of water and is left there while the sampler is being used. For example, a sampler may use a pneumatic pump that requires compressed air from a SCUBA tank. If the tank is left on the bottom, the length of the intake hose limits the diver to collecting samples in an area surrounding the tank. Also, some samplers use power sources that are not submergible and therefore must remain on shore or on a boat, using a cable to connect to the sampler.

Some samplers are hazardous for divers to use. For example, some samplers use air-driven power sources (such as drills) or air-driven pumps that use air from the diver's own air supply tank.

Some samplers require two hands for operation, for example, to arm or pump the device. Two-handed operation can make these samplers inconvenient and awkward to use when the hand not holding the sampler is occupied. Moreover, two-handed operation is a serious disadvantage, compromising diver safety, when the diver also needs to hold an item such as a lamp or light, or when the diver is required to read gauges or operate dive gear such as a buoyancy compensation device.

Some samplers are not continuous flow and therefore have limited sampling efficiency. Some samplers are restricted to a single sample or to a limited sample size, or have a difficult specimen transfer method.

Samplers that require pumping or constant rearming by the diver are labor intensive. Some even require multiple operators. For example, one operator may be required just to pump the sampler while another operator directs the intake hose. Also, samplers that must be manually armed/pumped may provide insufficient suction to capture certain organisms.

Samplers have been unable to take samples in many areas due to safety considerations or the type of substrate involved. Some underwater environments cannot be sampled due to safety concerns, including high velocity streams and water of low to zero visibility. Collecting samples from rock reef habitat is particularly difficult because of the inability of most samplers to gain access to surfaces with high rugosity. The same is true for heavily vegetated habitats. These types of areas can potentially be the most productive and unique habitats for benthic invertebrates (especially rare species) and larval fish.

The invention described herein avoids or ameliorates many of the shortcomings of current suction samplers mentioned above.

SUMMARY

In accordance with the invention, the above problems are solved by providing a portable, self-contained underwater suction sampler that collects solid, replicate biological samples in underwater environments. The suction sampler is submersible in water and is compact, small and lightweight compared to conventional samplers, and does not require connection to external equipment. Thus, the versatile sampler may be easily transported and used by one operator in a variety of underwater habitats, the mobility of the operator is increased when collecting samples, and the samples may be safely and rapidly collected using only one hand.

The term "self-contained" used herein means that the sampler is constructed so that all components are provided within a single device. No surface connections or connections to external equipment or power sources are necessary, rendering the sampler free to be manipulated without attached wires or cables. The term "compact" used herein means that the sampler is constructed so that all components are positioned in close proximity to one another. Such a handheld and cordless device is very portable, less cumbersome than conventional suction samplers, and allows the diver to more conveniently place the sampler in various orientations that are required to best sample a desired region.

In accordance with one embodiment of the invention, a compact, self-contained sampler for one-handed collection of aquatic biotic samples is provided. The sampler has a frame, a pump, a battery, and a switch. The pump has an intake tube attached to the frame and draws sample material into the intake tube. The battery is attached to the frame and is electrically connected to the pump. The switch is electrically connected to the pump and to the battery and is attached to the frame so that the operator can control activation of the pump with one hand. The pump, the battery, and the switch are all positioned on the frame in close proximity to one another to form a compact, self-contained unit.

In accordance with another embodiment of the invention, a compact, self-contained sampler for one-handed collection of aquatic biotic samples is provided. The sampler has a frame, a pump, a battery, a handle, a switch, and a sample collection reservoir. The pump has an intake tube attached to the frame and draws sample material into the intake tube. The battery is attached to the frame and is electrically connected to the pump. The handle is attached to the bottom of the frame so that a diver can hold the sampler in one hand. The switch is electrically connected to the pump and to the battery and is attached to the frame in close proximity to the handle so that the operator can control activation of the pump with one hand. The sample collection reservoir is connected to the pump to hold the sample material drawn into the intake tube. The pump, the reservoir, the battery, the handle, and the switch are all positioned in close proximity to one another to form a compact, self-contained unit.

In accordance with another embodiment of the invention, a method of collecting aquatic biotic samples using a suction sampler is provided. The method includes providing a frame; providing a pump with an intake tube attached to the frame to draw sample material into the intake tube; providing a battery attached to the frame and electrically connected to the pump to power the pump; providing a handle attached to a bottom of the frame for an operator to hold the sampler in one hand; providing an on/off pressure button electrically connected to the pump and to the battery and attached to the frame in close proximity to the handle for the operator to control activation of the pump with the one hand; providing a sample collection reservoir connected to the pump to hold the sample material drawn into the intake tube; placing the pump, the reservoir, the battery, the handle, and the pressure button in close proximity to one another to form a compact, self-contained unit; gripping the handle with a single hand; positioning the sampler in or on an area to be sampled; pushing the pressure button with the same single hand to turn on the pump, which creates suction through the intake tube to draw sample material into the intake tube and into the sample collection reservoir; and releasing the pressure button with the same single hand to turn off the pump after collecting the sample material.

In accordance with another embodiment of the invention, a method of collecting aquatic biotic samples using a suction sampler is provided. The method includes providing a frame, a pump with an intake tube, a battery, a handle, an on/off pressure button, and a sample collection reservoir; attaching, in close proximity to one another, the pump and the battery to the frame, the handle to a bottom of the frame, the pressure button to the frame near the handle, and the sample collection reservoir to the pump, to form a compact, self-contained unit, and electrically connecting together the battery, the pump, and the pressure button; gripping the handle with a single hand; positioning the sampler in or on an area to be sampled; while gripping the handle with the single hand, pushing the pressure button with the same single hand to turn on the pump, the pump creating suction through the intake tube to draw sample material into the intake tube and into the sample collection reservoir; releasing the pressure button with the same single hand to turn off the pump after collecting the sample material; and repeatedly pushing and releasing the pressure button with the single hand as desired to collect additional sample material.

Thus, the underwater suction sampler described herein gives diving scientists the ability to safely sample for aquatic biota on a variety of underwater substrates and under adverse environmental conditions, in support of biological assessments, surveys and monitoring studies including those used by the U.S. Environmental Protection Agency. The underwater suction sampler may be used to quantitatively and qualitatively collect attached periphyton, benthic invertebrates, aquatic plankton (such as zooplankton and ichthyoplankton), and sediments in underwater environments that were previously unable to be safely surveyed biologically by conventional samplers. Due to its compact size, the device may be safely used in high velocity streams and the unique ergonomic design allows samples to be taken in low to zero-visibility water conditions. The sampler is able to collect quantitative samples from rough, hard surfaces. It has a compact, self-contained design so that a diver can easily operate it with one hand, especially in adverse environmental conditions that require a diver to have one hand free for safe operation of dive equipment. The sampler also has a sufficiently light enough weight in water so as not to compromise the buoyancy and safety of the diver.

BRIEF DESCRIPTION OF THE DRAWINGS

Various aspects and advantages of the invention will become apparent from the following detailed description, taken in conjunction with the accompanying drawings, of which.

DETAILED DESCRIPTION

Figure 1:
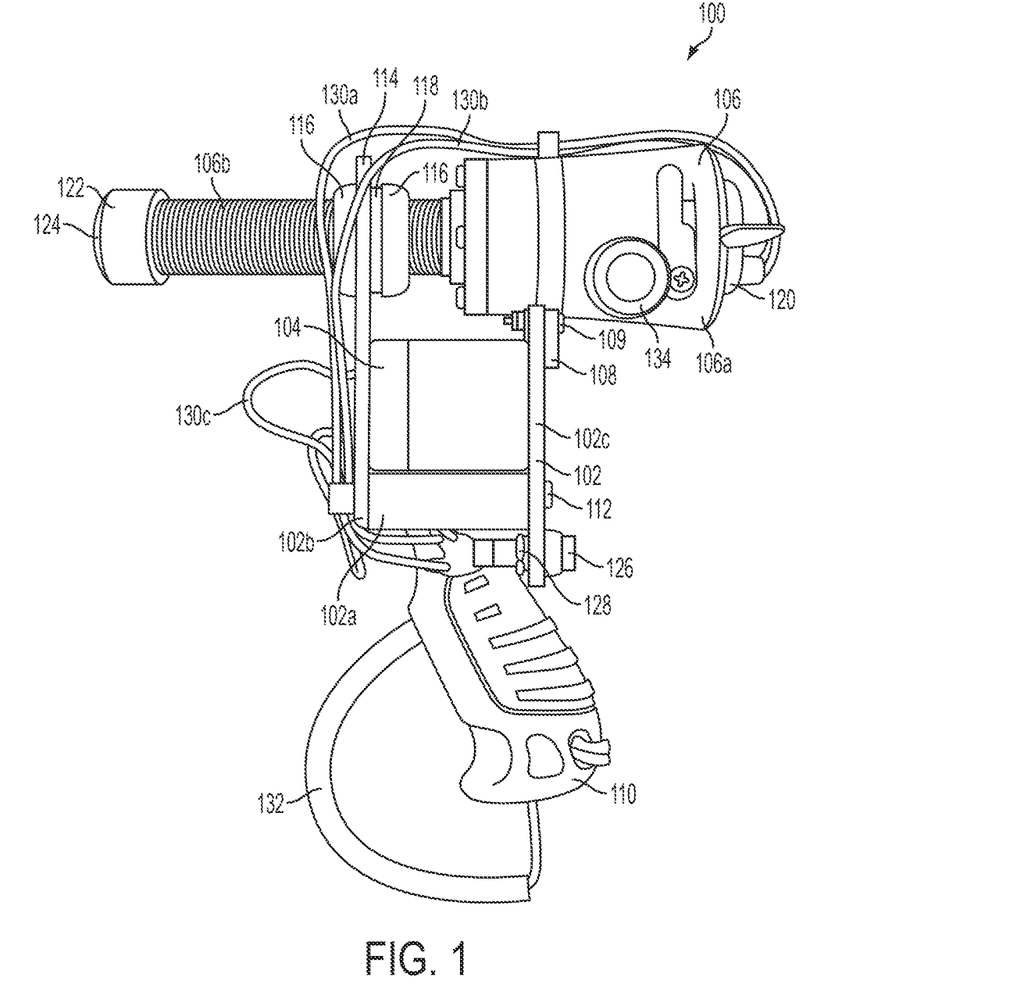
FIG. 1 shows a side view of a suction sampler embodying the principles of the invention.

The invention is a water-submersible suction sampler for collecting aquatic flora and fauna from underwater habitats. FIG. 1 shows a side view of a suction sampler 100 embodying the principles of the invention. As can be seen in FIG. 1, the suction sampler 100 has the general shape of a gun.

According to the embodiment shown in FIG. 1, the suction sampler 100 has a frame 102, a battery 104, a submersible pump 106 with a pump body 106a and an intake tube 106b, and a handle 110. The frame 102 has a base 102a, a first support member 102b, and a second support member 102c. The lower ends of the first support member 102b and the second support member 102c are attached to the base 102a using fasteners 112 such as stainless steel screws, washers, and locknuts. Alternatively, the frame 102 can be formed as an integral unit. The battery 104 is placed on top of the base 102a between the first support member 102b and the second support member 102c. In the preferred embodiment, the base 102a is a polycarbonate with about a ⅝-inch thickness, and the first support member 102b and the second support member 102c are polycarbonates with about ¼-inch thickness each. Also, in the preferred embodiment, the battery 104 is a rechargeable 12-volt, 1.3 amp-hour sealed, waterproof Werker® battery by Batteries Plus, LLC of Hartland, Wis., which has dimensions of about 95 mm (L)×50 mm (H)×41 mm (W). The battery 104 may be charged using a battery charger (not shown), such as an automatic, 12-V, 800 mA battery charger with charging monitoring circuitry by Power-Sonic Corporation of San Diego, Calif.

The upper end 114 of the first support member 102b has an opening through which the intake tube 106b of the submersible pump 106 is inserted. In the preferred embodiment, the pump 106 creates suction through the intake tube 106*b* via a sealed, rotating impeller (not shown) within the pump body 106*a*. Other types of pumps can be used if small enough to be attached to the frame 102 and if capable of being taken apart and cleaned under water without the use of tools. The intake tube 106*b* is secured to the first support member 102*b* using fasteners such as two nylon nuts 116 having a ¾-inch inner diameter and a rubber washer 118 having a ¾-inch inner diameter. The battery 104 is compression-fitted to the frame 102 by tightening the nylon nuts 116 on the intake tube 106*b* toward the pump body 106*a*. The pump body 106*a* is supported by the top of the second support member 102*c*. In the embodiment shown in FIG. 1, a pump bracket holder 108 is secured to the top of the second support member 102*c*. A bracket (not shown) on the bottom of the pump body 106*a* is placed within a slot (not shown) in the top of the pump bracket holder 108, and a pump bracket mounting plate 109 is placed over the pump bracket. The pump bracket is secured to the frame 102 by inserting a fastener through the pump bracket mounting plate 109, the pump bracket holder 108, and the second support member 102*c*. The pump bracket holder 108 and the pump bracket mounting plate 109 are polycarbonates with about ¼-inch thickness each. In the preferred embodiment, the pump 106 is a waterproof Mayfair 12-volt, 500 gallons/hour capacity, bait pump with a ¾-inch hose by Johnson Pumps of America of Hanover Park, Ill. The pump 106 shown in FIG. 1 has a cartridge 120 that contains a motor/impeller assembly (not shown). A mesh screen 200 (see FIG. 2) is placed over the end of the intake tube 106*b* of the pump 106 and held in place by a threaded collar 122, forming an intake nozzle 124 for the intake tube 106*b*. In the preferred embodiment, the mesh 200 is a 1-inch diameter plastic screen with 4-mm square mesh openings, and the threaded collar 122 is a PVC end fitting with ¾-inch female thread and ¹¹⁄₁₆-inch hole.

Figure 2:
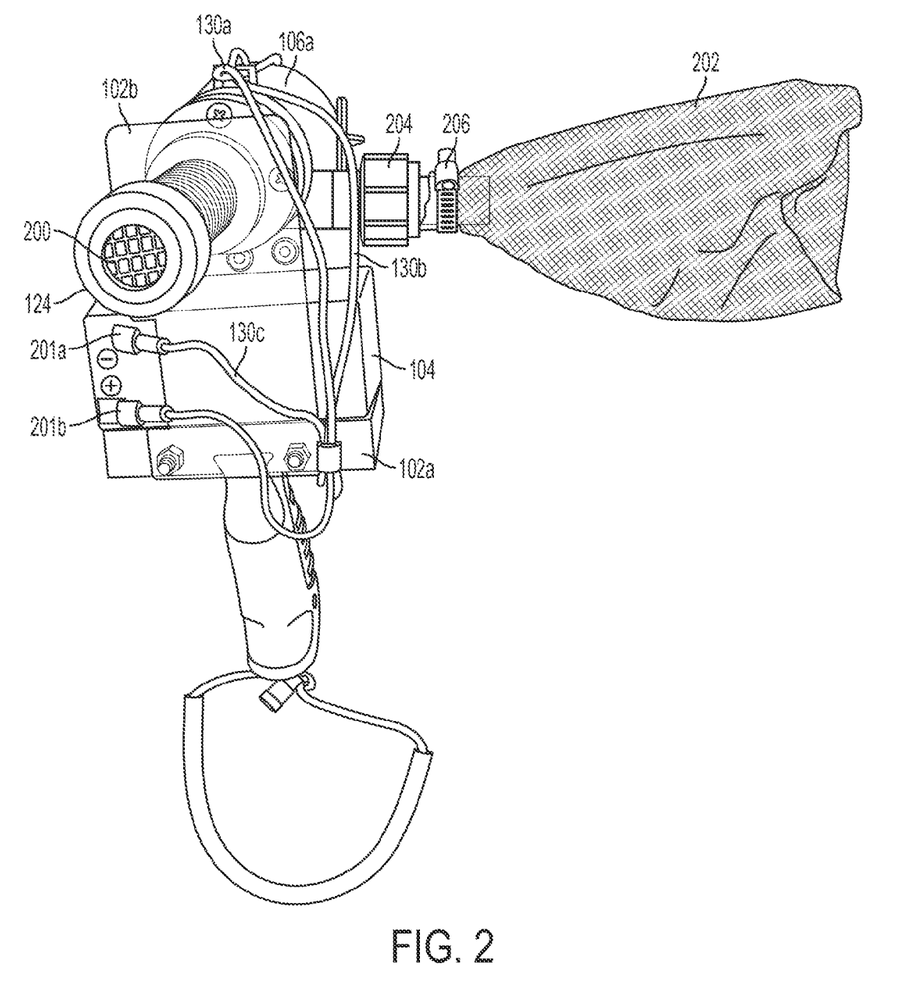
FIG. 2 shows a front perspective view of the suction sampler of FIG. 1 with a sample collection net attached to a pump.

A pressure switch 126 (also referred to herein as an "on/off pressure button") is attached to the lower end of the second support member 102*c* near its outer bottom edge by inserting the pressure switch 126 through a hole in the lower end of the second support member 102*c*. In the preferred embodiment, the pressure switch 126 is a panel-mount, spring-loaded, single pole, single throw (SPST) momentary pressure switch (3 A, 125 VAC), such as the Momentary Pushbutton Switch, model 275-1566 SPST, manufactured by Radio Shack of Fort Worth, Tex. The battery 104, the pressure switch 126, and the pump body 106*a* are electrically connected in series using three 18-gauge wires 130*a*, 130*b*, and 130*c*, and two terminal wire connectors 201*a* and 201*b* (see FIG. 2). For example, solderless, insulated, female 22-18 AWG terminal wire connectors may be used. As shown in FIGS. 1 and 2, wire 130*a* is connected to the pressure switch 126 and the pump body 106*a*, wire 130*b* is connected to the pump body 106*a* and the battery 104, and wire 130*c* is connected to the battery 104 and the pressure switch 126.

The handle 110, such as a plastic pistol grip handle manufactured by Underwater Kinetics of Poway, Calif., is attached to the bottom of the frame base 102*a* using set screws built into the handle 110. A lanyard 132 is attached to the bottom of the handle 110 for easy transportation of the suction sampler 100.

Samples are collected by being trapped and held in a detachable and removable sample collection reservoir, such as a net or a bottle or jar, which is attached externally to an exhaust tube 134 on the pump body 106*a*. FIG. 2 shows a front perspective view of the suction sampler 100 with a sample collection net 202 attached to the pump body 106*a*.

To attach the sample collection net 202 to the suction sampler 100, a connector 204 is connected to the exhaust tube 134 of the pump body 106*a*, and the sample collection net 202 is secured to the connector 204 using a fastener 206 such as a hose clamp. Particular embodiments of the invention may use a PVC fitting (¾-inch female thread to ¾-inch hose barb) for the connector 204, and a stainless steel hose clamp (size 10, 13-28 mm) for the fastener 206. The sample collection net 202 shown in FIG. 2 has a 230 µm mesh size, but size and mesh porosity can vary according to sampling design needs.

Figure 3:
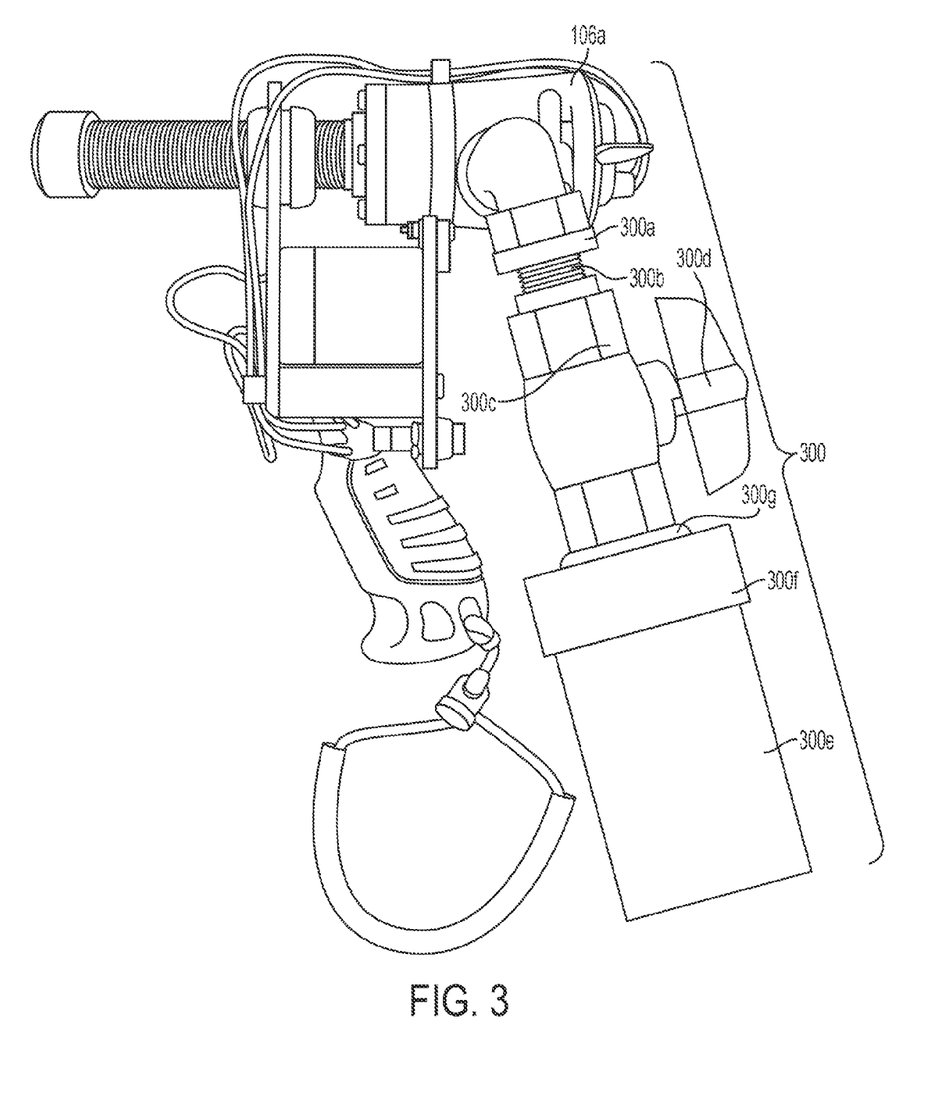
FIG. 3 shows a side view of the suction sampler of FIG. 1, including a sample collection jar assembly with a sample collection jar attached to a pump.
Figure 4:
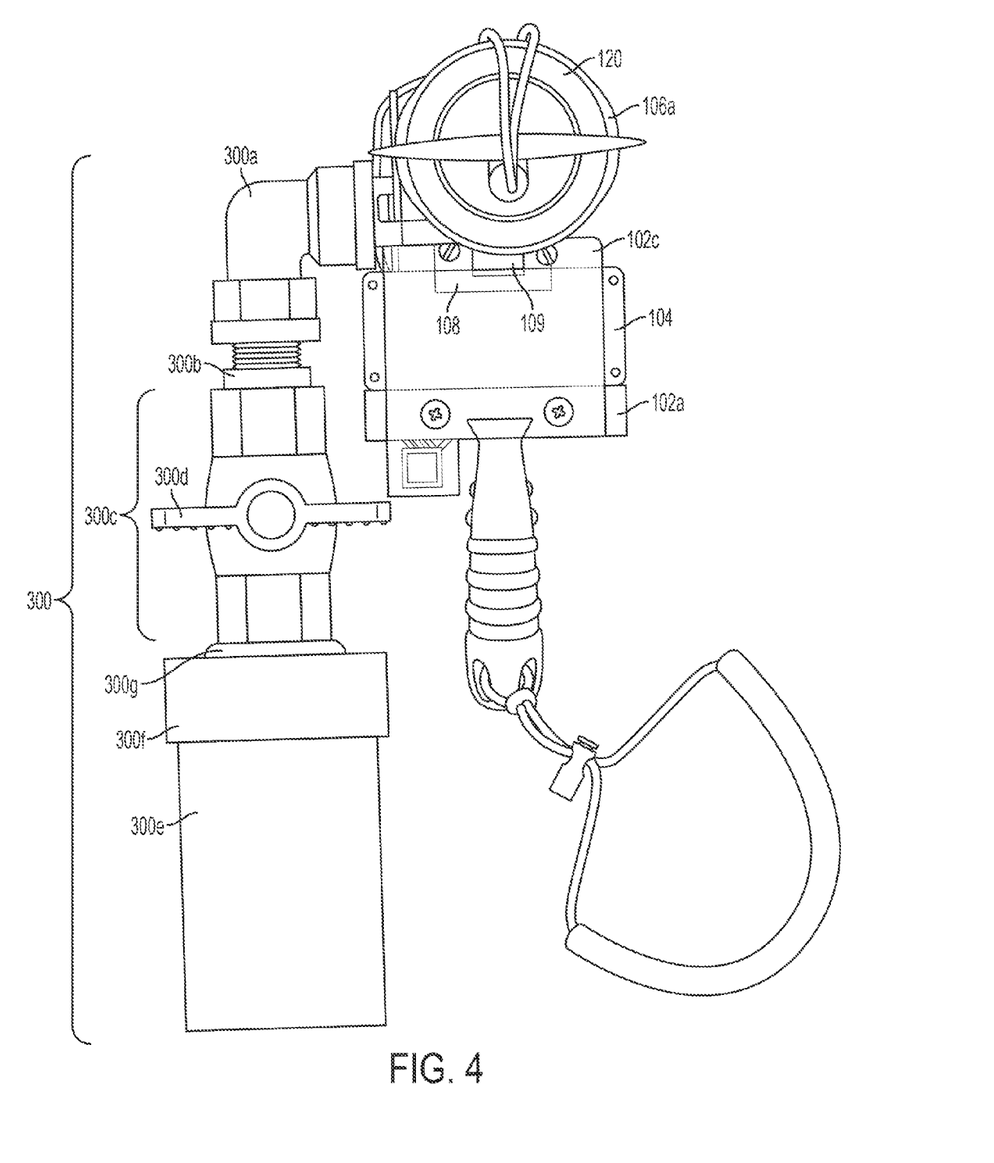
FIG. 4 shows a rear view of the suction sampler of FIG. 3.
Figure 5:
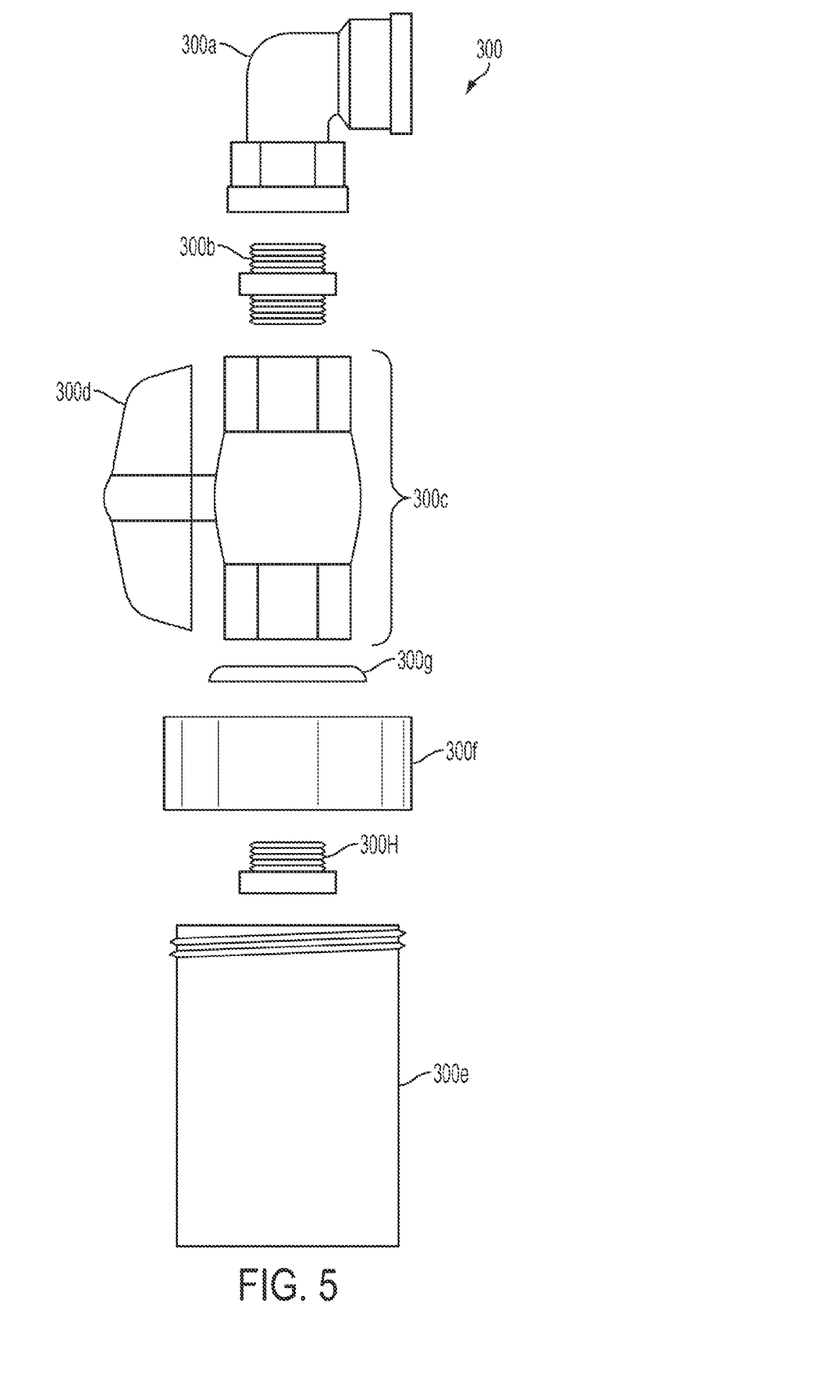
FIG. 5 shows an exploded view of the sample collection jar assembly shown in FIGS. 3 and 4.

Alternatively, FIG. 3 shows a side view of the suction sampler 100 with a sample collection jar assembly 300, rather than the sample collection net 202, attached to the pump body 106*a*. FIG. 4 shows a rear view of the suction sampler 100 with the sample collection jar assembly 300. FIG. 5 shows an exploded view of the sample collection jar assembly 300. Referring to FIGS. 3 to 5, the sample collection jar assembly 300 includes a first jar connector 300*a* that connects to the exhaust tube 134 on the pump body 106*a*, a second jar connector 300*b* that connects to the first jar connector 300*a*, a valve member 300*c* with a valve 300*d* that connects to the second jar connector 300*b*, and a sample collection jar 300*e* with a lid 300*f* that connects to the valve member 300*c*. Particular embodiments of the invention may use a PVC fitting (90-degree angle, ¾-inch×¾-inch threaded female) for the first jar connector 300*a*, a PVC fitting (¾-inch threaded male union) for the second jar connector 300*b*, and a PVC ball valve (¾-inch×¾-inch threaded female) for the valve member 300*c*.

Figure 6:
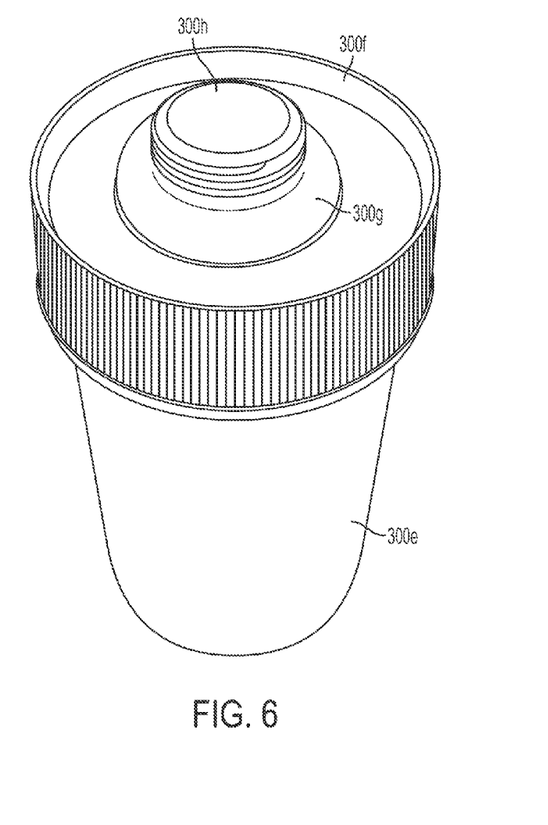
FIG. 6 shows a top perspective view of the sample collection jar shown in FIGS. 3 and 4.
Figure 7:
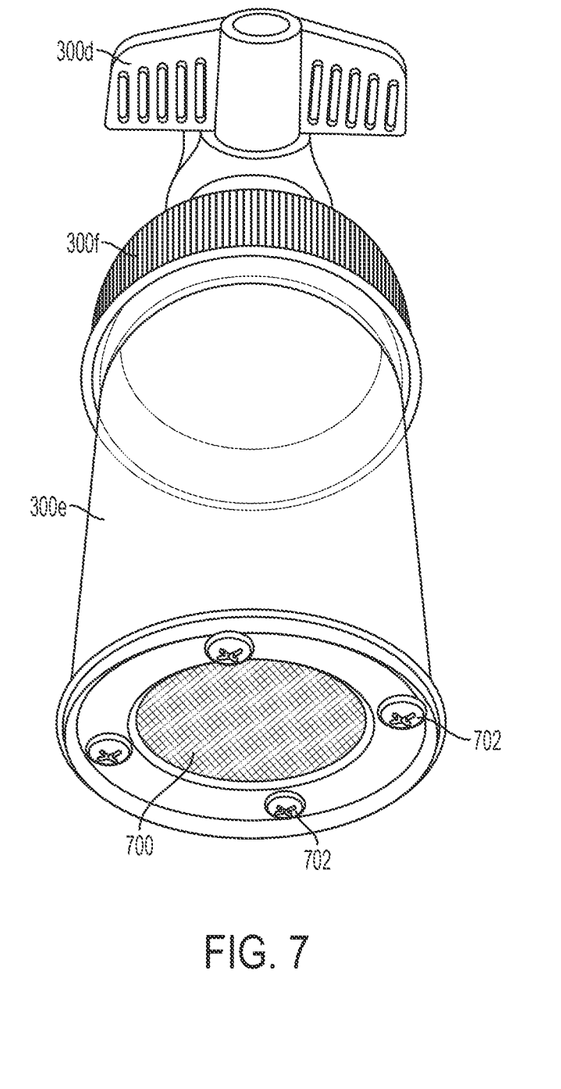
FIG. 7 shows a bottom perspective view of the sample collection jar shown in FIGS. 3 and 4.

FIG. 6 shows a top perspective view of the sample collection jar 300*e*. In the preferred embodiment, the sample collection jar 300*e* is a 120 ml Nalgene® sample jar (110 mm (H)×65 mm (diameter)) by Nalge Nunc International Corporation of Rochester, N.Y. The sample collection jar 300*e* has about a ¾-inch diameter hole cut in the center of the lid 300*f*. A fastener such as a ¾-inch inner diameter nylon nut 300*g* is placed on top of the lid 300*f* and a third jar connector 300*h* (such as a ¾-inch plastic nut/nipple) is inserted through the hole in the lid 300*f* and through the nylon nut 300*g* to connect the lid 300*f* to the valve member 300*c*. FIG. 7 shows a bottom perspective view of the sample collection jar 300*e*. The sample collection jar 300*e* has about a 40 mm diameter hole cut in the bottom of the jar 300*e*. A 230 µm stainless steel mesh cloth 700 is attached to the bottom of the sample collection jar 300*e* using fasteners 702 (such as screws and nuts) and is sealed to the bottom of the jar 300*e* using a silicone adhesive sealer. Rather than using separate components, the sample collection jar assembly 300 can be formed as an integral unit.

In particular embodiments, the suction sampler 100 is about 9 inches in length (i.e., approximately the length of the pump 106, including the pump body 106*a* and the intake tube 106*b*). In fresh water, the suction sampler 100 weighs about 1.25 pounds with the sample collection net 202 and about 1.5 pounds with the sample collection jar assembly 300. In air, the suction sampler 100 weighs about 3.4 pounds with the sample collection jar assembly 300 and about 2.8 pounds with the sample collection net 202.

To operate the suction sampler 100, the diver/operator grips the handle 110 with a single hand and directs the intake nozzle 124 of the intake tube 106*b* over or inside the area to be sampled, and pushes the pressure switch 126 to turn on the pump 106. If the sample collection reservoir used is the sample collection jar 300*e*, the operator opens the valve 300*d* on the valve member 300*c* before pushing the pressure switch 126. The pump 106 creates suction through the intake tube 106b, drawing the sample material into the pump 106 and depositing it into the sample collection reservoir. A sample is taken as long as the pressure switch 126 remains pushed by the diver/operator. The diver is free to carry the sampler to other areas, point the intake nozzle 124 exactly where he or she wants it to be positioned, and press and hold the pressure switch 126 as long as desired to collect additional samples without returning to the surface. Thus, the diver/operator can collect samples from different habitats during one diving event.

The area of each sample is calculated by measuring the area of the intake nozzle 124 using the formula Area=$\pi \times r^2$, where r is the radius of the intake nozzle 124. For example, the area of the intake nozzle 124 illustrated in FIG. 2 is about 227 mm$^2$. Multiple samples may be taken to form a composite sample. The area of the composite sample is calculated by multiplying the number of samples by the area of the individual sample.

The diver/operator can easily replace the sample collection reservoir while underwater diving to continue sampling without returning to the surface. If the sample collection reservoir used is the sample collection jar 300e, the diver/operator seals the sample collection jar 300e after the desired area is sampled by turning the valve 300d to the closed position. Replicate samples may be taken by detaching the collection jar assembly 300 from the pump body 106a and re-attaching an identical assembly to the pump body 106a.

The mesh screen 200 in the intake nozzle 124 minimizes clogging of the pump 106. If the mesh screen 200 becomes clogged with debris, the diver/operator simply brushes the mesh screen 200 to remove the clog. If the internal pump impellor becomes clogged, the diver/operator can easily remove the pump cartridge 120. The diver/operator then cleans debris from the impellor and replaces the cartridge 120.

Figure 8:
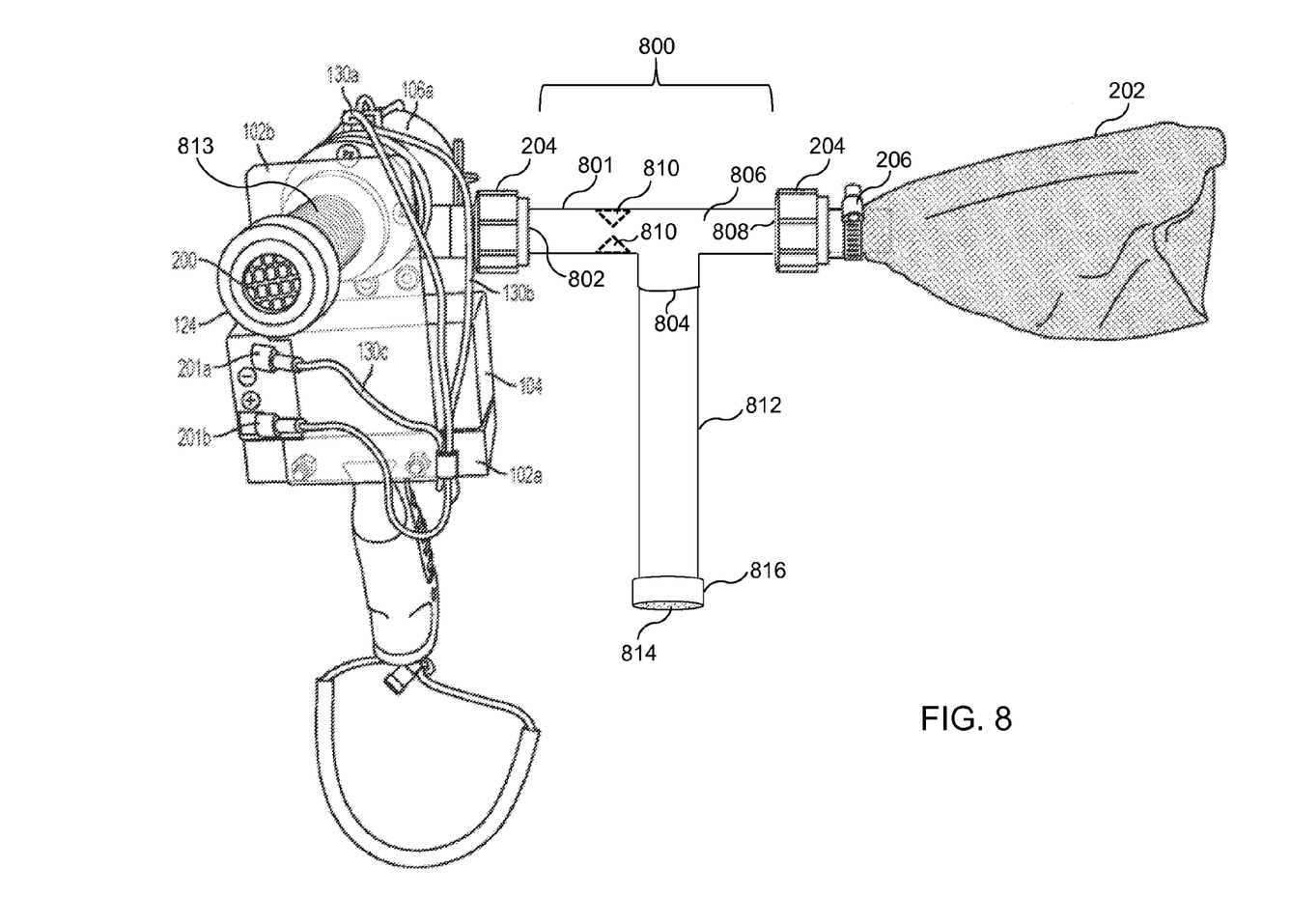
FIG. 8 shows a front perspective view of the suction sampler of FIG. 1 with a venturi tube attached to the sampler and a sample collection net attached to the venturi tube.

If the sample material is fragile, the sample collection reservoir may be attached to the suction sampler 100 so that the sample material does not enter the pump 106, as illustrated in the embodiment of the invention shown in FIG. 8. The embodiment of FIG. 8 includes a venturi tube assembly 800 with a venturi tube 801 having a water inlet port 802, a sample inlet port 804, a branch passage 806 with an outlet port 808, and internal flow constrictors 810. The water inlet port 802 is attached to the exhaust tube 134. A sample intake tube 812 is attached to the sample inlet port 804. The outlet port 808 of the branch passage 806 is attached to the sample collection reservoir, which in the embodiment of FIG. 8, is the sample collection net 202.

Attaching the venturi tube 801 to the exhaust tube 134 creates a siphon flow of water to the sample intake tube 812, with the intake tube 106b becoming a water intake tube 813. Thus, the venturi tube 801 diverts the sample material away from the pump 106, drawing the sample material into the sample intake tube 812 and into the sample collection reservoir.

Figure 9:
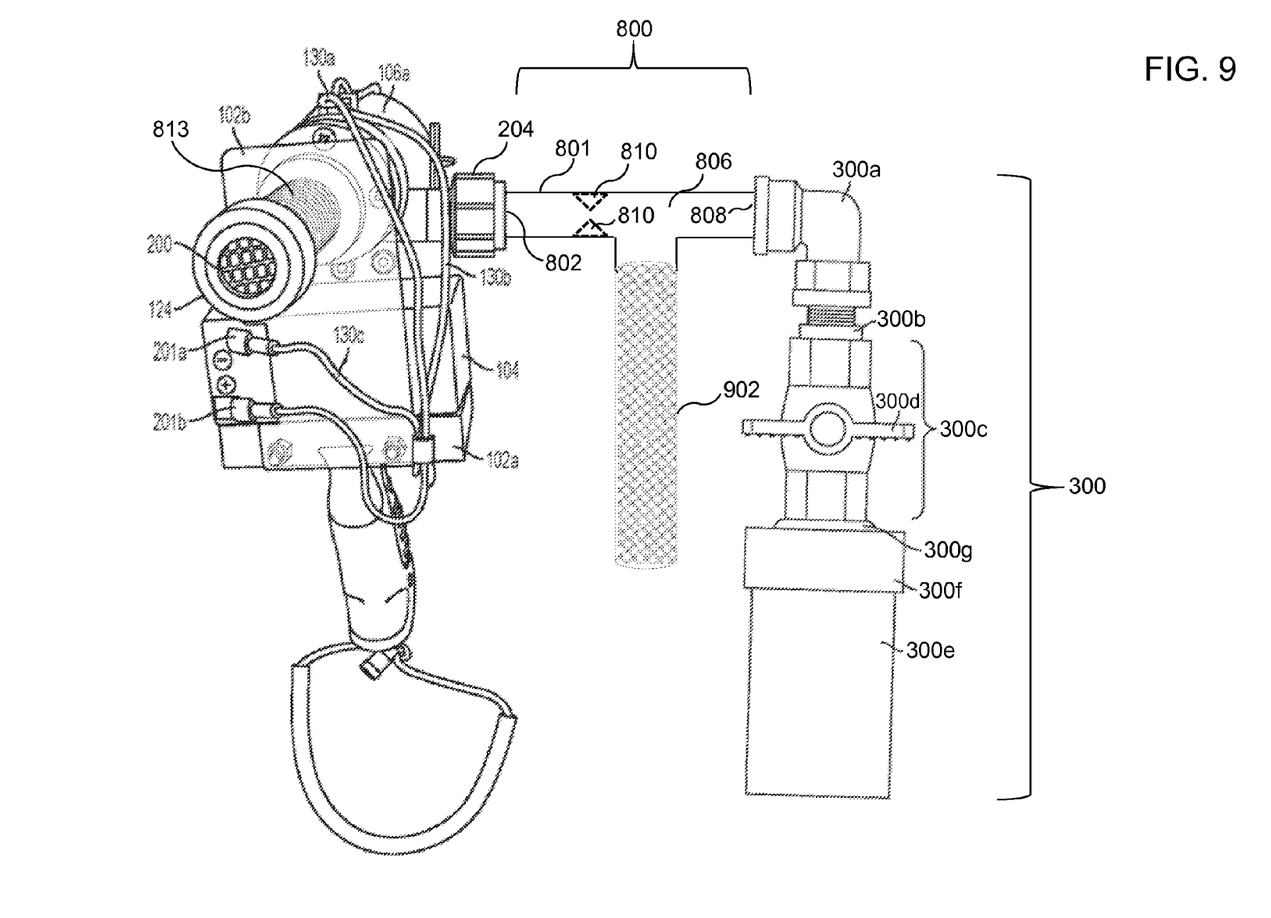
FIG. 9 shows a front perspective view of the suction sampler of FIG. 8 with a sample collection jar assembly attached to the venturi tube.

The sample intake tube 812 can be, for example, a PVC or stainless steel pipe, having a mesh screen 814 (similar to the mesh screen 200) placed over the end of the sample intake tube 812 that is held in place by a threaded collar 816 (similar to threaded collar 122) to form an intake nozzle for the sample intake tube 812. The sample intake tube 812 can also be constructed as a mesh 902, as shown in the embodiment of FIG. 9. In the embodiment shown in FIG. 9, the venturi tube 801 is connected to the sample collection jar assembly 300.

The hand-held underwater suction sampler described herein enables scientific divers to safely collect samples, both quantitative and qualitative, of small aquatic flora and fauna from a variety of substrates, including rock reef habitats and heavily vegetated habitats that can potentially be the most productive and unique habitats for benthic invertebrates (especially rare species) and larval fish. The compact size and the single-hand operation of this device allows it to be used in underwater environments that were previously considered unable to be sampled from due to safety concerns, including high velocity streams and water of low to zero visibility. The device described herein may be used under the previously described conditions in underwater habitats with, for example, submerged vegetation, silt/sand substrates, and in hard rock substrates.

From the description above, a number of advantages of some embodiments of the suction sampler become evident. These advantages include the following:

(a) The suction sampler can easily be used by divers because of its one-handed operation and small, compact size and weight (e.g., approximately 1.25 lbs. in water with the sample collection net), which does not compromise the safety of the diver via buoyancy changes.

(b) When the sample collection jar 300e is used during sampling, the diver uses two hands only when the valve 300d is turned on or off. If the sample collection net 202 is used, operation is entirely one-handed. The diver is not required to hold the suction sampler with both hands in order to pump/rearm the sampler, to hold external components, or to transport the suction sampler to different sampling locations.

(c) The suction sampler is completely submersible in water.

(d) The suction sampler allows scientists access to sample in areas that previously could not be sampled.

(e) The suction sampler is able to take continuous and multiple samples underwater from a variety of habitats for up to about thirty minutes of total activation time when a rechargeable 12-volt, 1.3 amp-hour sealed battery is used, without requiring the diver to return to the surface between samples.

(f) The sampler can safely collect invertebrates and periphyton in freshwater up to about 30 feet in depth and in water temperatures as low as about 49° F.

(g) The pump's motor/impellor assembly can be taken apart and cleaned underwater even under adverse conditions.

(h) The large-handled valve (approximately 90 mm in the embodiment shown in FIG. 4) on the sample collection jar allows divers to operate the valve while wearing thick, thermal protective gloves.

(i) The suction sampler can also be used by non-divers to collect plankton or sediment samples while wading in streams over a diversity of substrates. It could also be used to collect fine ferrous metal particles (i.e., gold dust) by attaching magnets to the inside of the sample jar.

(j) The suction sampler is self-contained, compact, and highly portable both during transportation to and from sampling areas and during operation/activation, and does not require external connections to power sources, air sources, etc. The highly portable and gun-shaped sampler can be directed to a specific target and can also reach into difficult to reach areas. The one-handed collection capability of the hand-held sampler, with its projecting intake tube, allows the diver to place the sampler in various orientations that are required to best sample a desired region. This allows the diver access to sample in areas that previously could not be sampled, such as surfaces with high rugosity (e.g., rock reef habitats) or heavily vegetated habitats. Thus, the sampler can take multiple samples from a variety of underwater habitats.

Although the invention has been described relative to specific embodiments thereof, it is not so limited and many modifications and variations thereof will be readily apparent to those skilled in the art in the light of the above teachings. For example, while the suction sampler 100 takes spatially quantitative samples, quantitative temporal results can be achieved, with the addition of a switch-activated timer or counter (not shown), by calculating flow rate over time. The counter would be placed within a waterproof housing and mounted on the second support member 102c, for example, next to the pressure switch 126. The combination of the pressure switch 126 and the counter would form the switch-activated timer. A Red Lion model CUB4L000, 12 VDC, bipolar, reflective LCD miniature electronic counter manufactured by Red Lion Controls, Inc. of York, Pa. may be used for the counter. The counter would be connected to wire 130a, which connects the pressure switch 126 to the pump motor body 106a. The counter would record the amount of time the pressure switch 126 is pressed and, thus, the amount of time the sampler is activated. With the addition of the timer, the suction sampler can be used to make scientific samples for estimating catch-per-unit-effort (CPUE), which is commonly used in ecological studies such as those developed in rapid bioassessment protocols (RBPs) by government agencies, including the U. S. Environmental Protection Agency (USEPA). The USEPA's RBP for streams and rivers is used to analyze habitat and biological measurements to assess biotic communities and the overall condition of the streams and rivers.

Thus, it will be appreciated by those skilled in the art that modifications and variations of the present invention are possible without departing from the principles and spirit of the invention, the scope of which is defined in the appended claims and their equivalents.

LIST OF REFERENCE NUMERALS 100 suction sampler
102 frame
102a base of frame
102b first support member of frame
102c second support member of frame
104 battery
106 pump
106a pump body
106b intake tube
108 pump bracket holder
109 pump bracket mounting plate
110 handle
112 fasteners (for frame)
114 upper end of first support member
116 nylon nut
118 washer
120 pump cartridge
122 threaded collar
124 intake nozzle
126 pressure switch
128 fasteners (for pressure switch)
130a wire cable
130b wire cable
130c wire cable
132 lanyard
134 exhaust tube
200 mesh (for intake nozzle)
202 sample collection net
204 connector (for sample collection net)
206 fastener (for sample collection net)
201a terminal wire connector
201b terminal wire connector
300 collection jar assembly
300a first jar connector
300b second jar connector
300c valve member
300d valve
300e sample collection jar
300f lid (of sample collection jar)
300g nylon nuts
300h third jar connector
700 mesh (for sample collection jar)
702 fasteners (for attaching mesh to sample collection jar)
800 venturi tube assembly
801 venturi tube
802 water inlet port of venturi tube
804 sample inlet port of venturi tube
806 branch passage of venturi tube
808 outlet port of venturi tube
810 internal flow constrictors of venturi tube
812 sample intake tube (for venturi tube)
813 water intake tube
814 mesh screen (for venturi sample intake tube)
816 threaded collar (for venturi sample intake tube)
902 mesh tube (for venturi sample intake tube)

What is claimed is:

1. A sampler for collection of aquatic biotic samples, comprising:
a frame; a pump having an exhaust tube, and a water intake tube attached to the frame, the pump drawing water into the water intake tube; a battery attached to the frame and electrically connected to the pump to power the pump; a handle attached to a bottom of the frame for an operator to hold the sampler in one hand; a switch electrically connected to the pump and to the battery and attached to the frame in close proximity to the handle for the operator to control activation of the pump with the one hand; a venturi tube assembly having a sample intake tube, a venturi tube with a water inlet port, a sample inlet port, and a branch passage with an outlet port, the water inlet port being attached to the exhaust tube and the sample intake tube being attached to the sample inlet port; and a sample collection reservoir connected to the outlet port, wherein the pump draws sample material into the sample intake tube and the venturi tube diverts the sample material away from the pump and into the sample collection reservoir to prevent damage to the sample material.

2. The sampler of claim 1, wherein the frame comprises: a base on which the battery is placed, the base having a first side and a second side; a first support member having an upper end with a hole and a lower end, the lower end of the first support member being attached to the first side of the base and the upper end of the first support member receiving the water intake tube of the pump through the hole; and a second support member having an upper end and a lower end, the lower end of the second support member being attached to the second side of the base, and the base, the first support member, and the second support member forming a receptacle for the battery.

3. The sampler of claim 1, wherein the sampler is submersible in water.

4. The sampler of claim 1, wherein the pump is a 12-volt, 500 gallons/hour capacity, bait pump.

5. The sampler of claim 1, further comprising an intake nozzle on an open end of the sample intake tube of the pump, the nozzle having a mesh screen and a threaded collar placed on the open end to hold the mesh screen in place over the open end.

6. The sampler of claim 5, wherein the mesh screen has 4-mm square mesh openings.

7. The sampler of claim 1, wherein the switch is a panel-mount, spring-loaded, single pole, single throw (SPST) momentary pressure switch.

8. The sampler of claim 1, wherein the sample collection reservoir is a detachable sample collection jar.

9. The sampler of claim 1, wherein the sample collection reservoir is a detachable sample collection net.

10. The sampler of claim 9, wherein the sampler has a length of about 9 inches and a weight of about 1.25 lbs. in water with the sample collection net.

11. The sampler of claim 1, wherein the switch is a switch-activated timer to record the amount of time the sampler is activated.

12. A method of collecting aquatic biotic samples using a suction sampler, comprising:
providing a frame, a pump with an exhaust tube and a water intake tube, a battery, a handle, an on/off pressure button, a venturi tube assembly with a sample intake tube, and a sample collection reservoir; attaching, in close proximity to one another, the pump and the battery to the frame, the handle to a bottom of the frame, the pressure button to the frame near the handle, the venturi tube assembly to the exhaust tube, and the sample collection reservoir to the venturi tube assembly, to form a compact, self-contained unit, and electrically connecting together the battery, the pump, and the pressure button; gripping the handle with a single hand;
positioning the sampler in or on an area to be sampled; while gripping the handle with the single hand, pushing the pressure button with the same single hand to turn on the pump, the pump creating suction through the water intake tube and the sample intake tube to draw sample material into the sample intake tube, the venturi tube assembly diverting the sample material away from the pump and into the sample collection reservoir to prevent damage to the sample material; releasing the pressure button with the same single hand to turn off the pump after collecting the sample material; and
repeatedly pushing and releasing the pressure button with the single hand as desired to collect additional sample material.

13. A sampler for collection of aquatic biotic samples, comprising:
a frame; a pump, with an exhaust tube, attached to the frame; a battery attached to the frame and electrically connected to the pump to power the pump; a switch electrically connected to the pump and to the battery and attached to the frame for an operator to control activation of the pump with one hand; and a venturi tube assembly having a sample intake tube, the venturi tube assembly being attached to the exhaust tube, wherein the pump draws sample material into the sample intake tube and the venturi tube assembly diverts the sample material away from the pump to prevent damage to the sample material; wherein the venturi tube assembly further comprises a venturi tube with a water inlet port, a sample inlet port, and a branch passage with an outlet port, wherein the water inlet port is attached to the exhaust tube and the sample intake tube is attached to the sample inlet port.

14. The sampler of claim 13, further comprising a sample collection reservoir connected to the outlet port to hold the sample material drawn into the sample intake tube.

15. The sampler of claim 14, wherein the sample collection reservoir is a detachable sample collection jar.

16. The sampler of claim 14, wherein the sample collection reservoir is a detachable sample collection net.

17. The sampler of claim 13, wherein the pump further comprises a water intake tube, the pump drawing water into the water intake tube and through the venturi tube.

18. The sampler of claim 13, further comprising a handle attached to a bottom of the frame in close proximity to the switch for the operator to hold the sampler in one hand and control activation of the pump with the one hand.

* * * * *